United States Patent
Shah et al.

(10) Patent No.: US 9,080,932 B2
(45) Date of Patent: Jul. 14, 2015

(54) ELECTRONIC DEVICE WITH PRINTED CIRCUIT BOARD STRESS MONITORING

(71) Applicant: Apple Inc., Cupertino, CA (US)

(72) Inventors: Dhaval N. Shah, Fremont, CA (US); Shayan Malek, San Jose, CA (US); Vivek Katiyar, Los Gatos, CA (US)

(73) Assignee: Apple Inc., Cupertino, CA (US)

( * ) Notice: Subject to any disclaimer, the term of this patent is extended or adjusted under 35 U.S.C. 154(b) by 201 days.

(21) Appl. No.: 13/892,748

(22) Filed: May 13, 2013

(65) Prior Publication Data

US 2014/0331741 A1    Nov. 13, 2014

(51) Int. Cl.
*G01N 3/30*  (2006.01)
*G01M 99/00*  (2011.01)
*G01N 3/303*  (2006.01)
*G01N 33/00*  (2006.01)

(52) U.S. Cl.
CPC ............ *G01N 3/30* (2013.01); *G01M 99/00* (2013.01); *G01N 3/303* (2013.01); *G01N 2033/0078* (2013.01)

(58) Field of Classification Search
CPC ..... G01P 15/0891; G01P 15/18; G01P 1/127; G01L 5/0052; G11B 19/043; G11B 19/042; H04M 2250/12
USPC ........................................ 73/12.06
See application file for complete search history.

(56) References Cited

U.S. PATENT DOCUMENTS

| | | | |
|---|---|---|---|
| 7,059,182 B1* | 6/2006 | Ragner | 73/200 |
| 7,096,748 B2* | 8/2006 | Kutlu | 73/862.474 |
| 8,061,182 B2* | 11/2011 | Weber et al. | 73/12.06 |
| 8,145,441 B2* | 3/2012 | Xi | 702/41 |
| 8,310,457 B2* | 11/2012 | Faubert et al. | 345/173 |
| 8,330,305 B2* | 12/2012 | Hart et al. | 307/650 |
| 8,549,892 B2* | 10/2013 | Weber et al. | 73/12.06 |
| 2006/0021453 A1* | 2/2006 | Kutlu | 73/862.474 |
| 2009/0132197 A1* | 5/2009 | Rubin et al. | 702/141 |
| 2009/0195394 A1* | 8/2009 | Johnson et al. | 340/584 |
| 2010/0042322 A1 | 2/2010 | Won | |
| 2010/0319434 A1* | 12/2010 | Weber et al. | 73/12.06 |
| 2011/0075384 A1 | 3/2011 | Yeates | |
| 2011/0288448 A1 | 11/2011 | Sanders et al. | |
| 2012/0265028 A1 | 10/2012 | Hughes et al. | |
| 2013/0054180 A1* | 2/2013 | Barfield | 702/138 |

FOREIGN PATENT DOCUMENTS

WO    2007066853    6/2007

\* cited by examiner

*Primary Examiner* — Freddie Kirkland, III
(74) *Attorney, Agent, or Firm* — Treyz Law Group; G. Victor Treyz; Joseph F. Guihan

(57) ABSTRACT

An electronic device may contain electrical components mounted on one or more substrates such as printed circuit boards. During a drop event, the printed circuit boards and components may be subjected to stresses. Strain gauges may be formed from metal traces embedded within dielectric layers in the printed circuit boards. The strain gauges may be used to make stress measurements at various locations on the boards. Stress data may be collected in response to data from an accelerometer indicating that the device has been dropped. Stress data collection may be halted in response to determining that the device has struck an external surface. Impact may be detected using accelerometer data, strain gauge output, or other sensor data. Stress data may be analyzed by the electronic device or external equipment.

20 Claims, 9 Drawing Sheets

ELECTRONIC DEVICE WITH PRINTED CIRCUIT BOARD STRESS MONITORING

BACKGROUND

This relates to electronic devices and, more particularly, to gathering stress data in electronic devices.

Electronic devices such as cellular telephones and other portable devices are sometimes subjected to considerable stresses. As an example, components on a printed circuit board in an electronic device may be subjected to high levels of stress during a drop event or other undesired impact. The stress imparted on a device during this type of scenario may cause integrated circuit solder joints and other structures to fail, leading to reliability problems.

Without accurate information on the stresses that occur within an electronic device, it can be difficult or impossible to troubleshoot device failures. This can make it challenging to repair devices and to improve device designs to prevent future problems.

SUMMARY

An electronic device may contain electrical components mounted on one or more substrates such as printed circuit boards. The electrical components may include integrated circuits, discrete components such as capacitors, resistors, and inductors, switches, connectors, sensors, input-output devices such as status indicators lights, audio components, and other electrical and mechanical components.

When a user drops the electric device, the printed circuit boards and components may be subjected to large stresses. Strain gauges may be formed from metal traces embedded within dielectric layers in the printed circuit boards. The strain gauges may be used to make stress measurements at various locations on the boards. For example, the strain gauges may be used to measure how much stress is being imparted to different portions of a printed circuit board and to the electrical components on the printed circuit board.

Stress data may be collected in storage such as a circular buffer. The collection of stress data may be initiated in response to data from an accelerometer indicating that the device has been dropped. Stress data collection may be halted in response to determining that the device has struck an external surface. Impact may be detected using accelerometer data, strain gauge output, or other sensor data.

Stress data may be analyzed by the electronic device or external equipment. For example, stress data may be analyzed in real time to present alerts to the user, may be analyzed with a service center computer to provide service center personnel with guidance for repairing the electronic device, or may be analyzed by computing equipment of a manufacturer to help revise the design of the electronic device.

Further features, their nature and various advantages will be more apparent from the accompanying drawings and the following detailed description of the preferred embodiments.

DETAILED DESCRIPTION

Electronic devices may contain electrical components such as integrated circuits, connectors, switches, sensors, and other circuitry. Solder joints, cable connections, metal interconnect traces on printed circuit boards, and other conductive paths within an electronic device are used to convey signals between components. When subjected to stress during a drop event, this circuitry can be damaged. As an example, solder joints may crack and become unreliable, integrated circuits may become damaged, and metal traces may split apart or may exhibit cracks that change their conductive properties. Pins in a connector can be bent and structures such as switches, discrete components such as resistors, inductors, and capacitors, and other electronic structures in a device may become damaged. Damage may prevent a device from working properly or may make a device fragile and prone to future failures.

To provide device 10 with the ability to monitor stress from impacts during drop events, other sharp impacts, and other movement that may impart damage, device 10 may be provided with sensors. The sensors may include one or more strain gauges embedded within one or more printed circuit boards or other substrates, may include one or more packaged strain gauges mounted to printed circuits or other substrates, may include an accelerometer or other sensor that is mounted on a printed circuit board, or may include other sensors.

Figure 1:
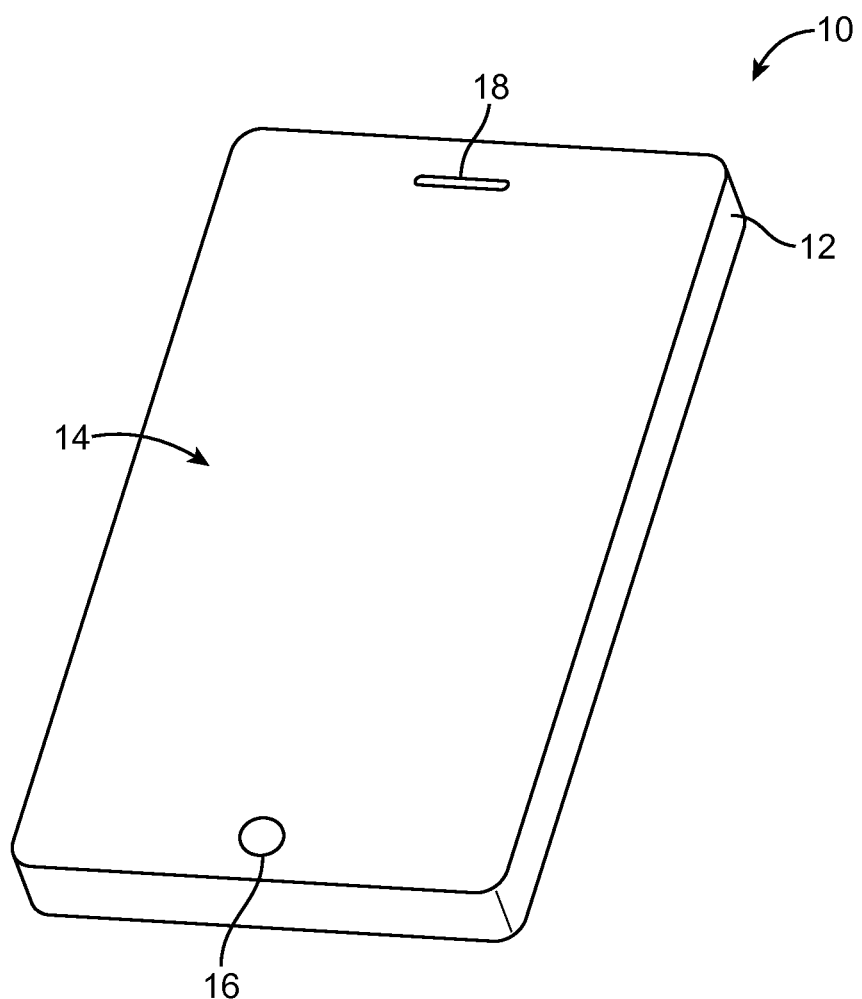
FIG. 1 is a perspective view of an illustrative portable electronic device that may be provided with stress sensing capabilities in accordance with an embodiment.

An illustrative electronic device of the type that may include strain gauges or other sensors for providing stress sensing functionality and other data gathering capabilities is shown in FIG. 1. Device 10 of FIG. 1 may be a handheld device such as a cellular telephone or media player, a tablet computer, a notebook computer, or other portable electronic device, a wearable or miniature device such as a wristwatch or pendant device, a television, a computer monitor, or other electronic equipment.

As shown in FIG. 1, electronic device 10 may include a display such as display 14. Display 14 may be a touch screen that incorporates a layer of conductive capacitive touch sensor electrodes or other touch sensor components or may be a display that is not touch-sensitive. Display 14 may include an array of display pixels formed from liquid crystal display (LCD) components, an array of electrophoretic display pixels, an array of electrowetting display pixels, an array of organic light-emitting diode display pixels, or display pixels based on other display technologies.

Display 14 may be protected using a display cover layer such as a layer of transparent glass or clear plastic. Openings may be formed in the display cover layer. For example, an opening may be formed in the display cover layer to accommodate a button such as button 16 and an opening such as opening 18 may be used to form a speaker port. Device configurations without openings in display 14 may also be used for device 10.

Device 10 may have a housing such as housing 12. Housing 12, which may sometimes be referred to as an enclosure or case, may be formed of plastic, glass, ceramics, fiber composites, metal (e.g., stainless steel, aluminum, etc.), other suitable materials, or a combination of any two or more of these materials.

Housing 12 may be formed using a unibody configuration in which some or all of housing 12 is machined or molded as a single structure or may be formed using multiple structures (e.g., an internal frame structure, one or more structures that form exterior housing surfaces, etc.). Openings may be formed in housing 12 for data ports, speaker ports, microphone ports, camera windows, antenna windows, buttons, and other components (as examples).

Figure 2:
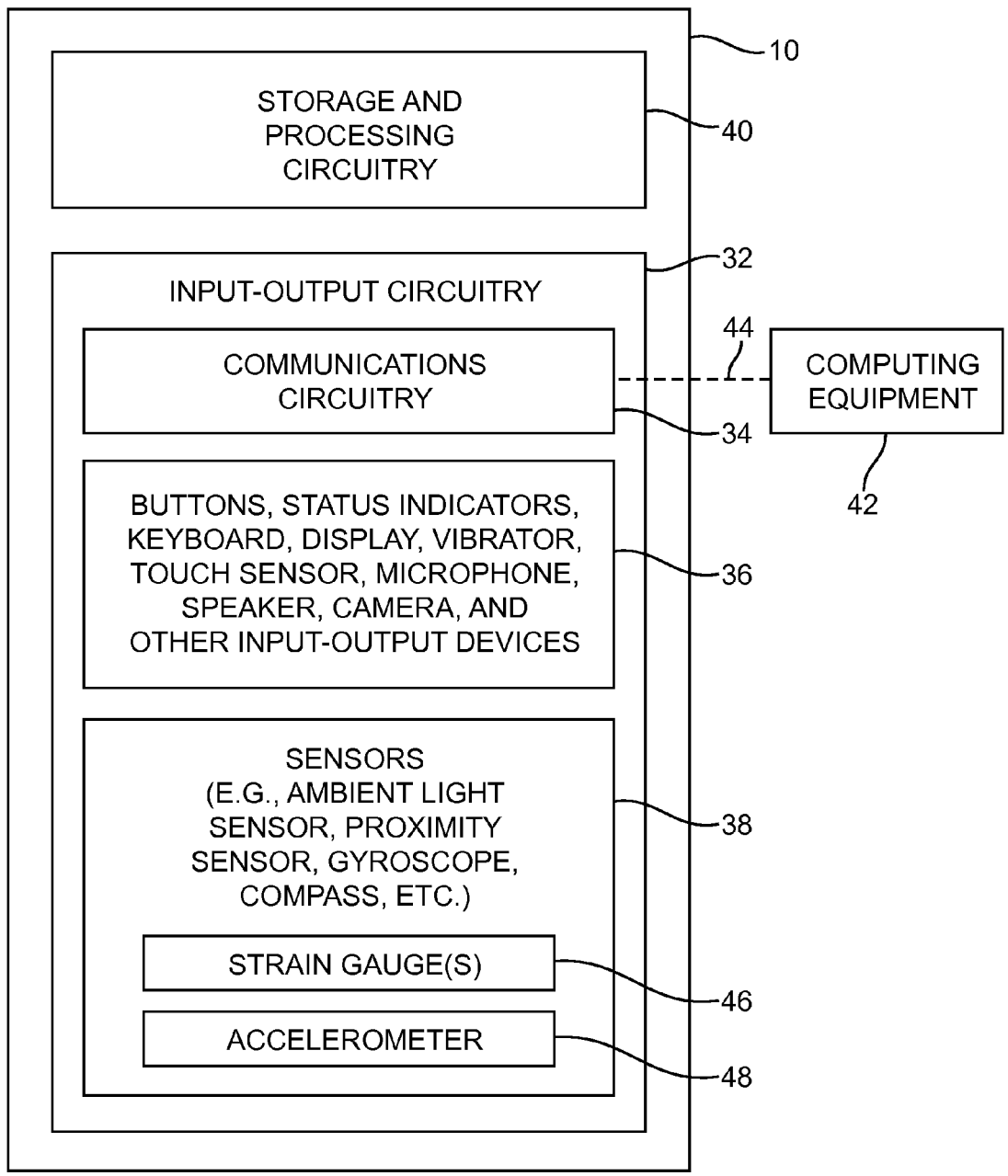
FIG. 2 is a schematic diagram of an illustrative electronic device such as the portable electronic device of FIG. 1 in accordance with an embodiment.

A schematic diagram of device 10 showing how device 10 may include sensors and other components is shown in FIG. 2. As shown in FIG. 2, electronic device 10 may include control circuitry such as storage and processing circuitry 40. Storage and processing circuitry 40 may include one or more different types of storage such as hard disk drive storage, nonvolatile memory (e.g., flash memory or other electrically-programmable-read-only memory), volatile memory (e.g., static or dynamic random-access-memory), etc. Processing circuitry in storage and processing circuitry 40 may be used in controlling the operation of device 10. The processing circuitry may be based on a processor such as a microprocessor and other suitable integrated circuits. With one suitable arrangement, storage and processing circuitry 40 may be used to run software on device 10, such as internet browsing applications, email applications, media playback applications, operating system functions, software for capturing and processing images, software implementing functions associated with gathering and processing sensor data such as stress data, etc.

Input-output circuitry 32 may be used to allow data to be supplied to device 10 and to allow data to be provided from device 10 to external devices.

Input-output circuitry 32 may include wired and wireless communications circuitry 34. Communications circuitry 34 may include radio-frequency (RF) transceiver circuitry formed from one or more integrated circuits, power amplifier circuitry, low-noise input amplifiers, passive RF components, one or more antennas, and other circuitry for handling RF wireless signals. Wireless signals can also be sent using light (e.g., using infrared communications). Using communications circuitry 34, device 10 may communicate with external equipment such as computing equipment over communications path 44. Communications path 44 may be a wired or wireless communications link or may include both wired and wireless paths. Computing equipment 42 may be a server or other computing equipment that is coupled to device 10 through the internet and/or other networks, may be a host computer that is coupled to device 10 through a wired cable or a wireless local area network wireless path (or a peer-to-peer wireless link), may be a network of one or more computers, may be a peer device, may be a kiosk, may be equipment embedded within a larger system, may include multiple different types of computing equipment, or may include other suitable electronic equipment. If desired, different pieces of equipment 42 may be coupled to device 10 at different times.

Input-output circuitry 32 may include input-output devices 36 such as button 16 of FIG. 1, joysticks, click wheels, scrolling wheels, a touch screen such as display 14 of FIG. 1, other touch sensors such as track pads or touch-sensor-based buttons, vibrators, audio components such as microphones and speakers, image capture devices such as a camera module having an image sensor and a corresponding lens system, keyboards, status-indicator lights, tone generators, key pads, and other equipment for gathering input from a user or other external source and/or generating output for a user.

Sensor circuitry such as sensors 38 of FIG. 2 may include an ambient light sensor for gathering information on ambient light levels and a proximity sensor such as a capacitive proximity sensor or infrared-light-based proximity sensor. Sensors 38 may also include a pressure sensor, a temperature sensor, an accelerometer such as accelerometer 48, a gyroscope, a compass, stress sensing circuitry such as one or more strain gauges 46, and other sensors for making measurements associated with device 10. Components such as cameras and microphones may be used as visual and audio sensors, respectively.

Strain gauges, which may sometimes be referred to as stress sensors, may be implemented using stand-alone units (e.g., strain gauges packaged in surface mount technology packages or other packages) or may be implemented from patterned metal supported by a substrate. The patterned metal may be formed from stamped metal foil, patterned metal traces, or other metallic materials. Patterned metal for strain gauges may be supported by dielectric structures such as a plastic carrier, a layer of glass, ceramic structures, a printed circuit such as a rigid printed circuit board (e.g., a printed circuit board formed from one or more layers of fiberglass-filled epoxy such as FR4), or other dielectric materials. Using the strain gauges in device 10, device 10 can monitor for the occurrence of stress that may affect device reliability or that could result in a failure requiring repair.

Figure 3:
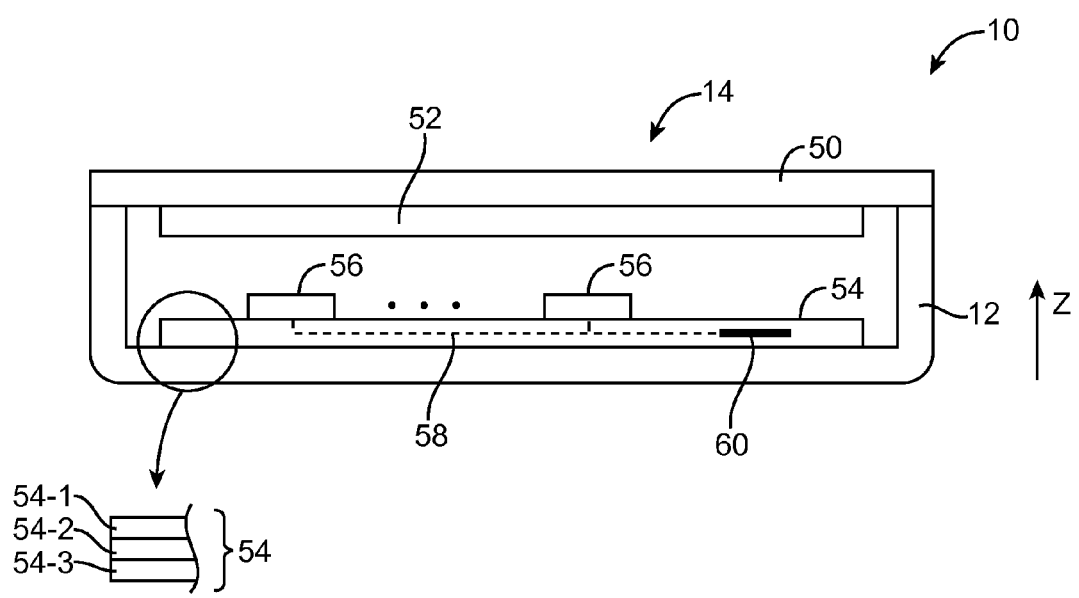
FIG. 3 is a cross-sectional side view of an illustrative electronic device having electronic components mounted on a substrate such as a printed circuit having strain gauge structures such as strain gauge structures embedded within the printed circuit in accordance with an embodiment.

A cross-sectional side view of device 10 is shown in FIG. 3. As shown in the illustrative configuration of FIG. 3, device 10 may have a display such as display 14 that is mounted on the front face of device 10. Display 14 may have a display cover layer 50 and a display module such as display module 52. Display module 52 may be, for example, a liquid crystal display module or an organic light-emitting diode display layer (as examples).

Device 10 may include components such as components 56 that are mounted on one or more printed circuit boards such as printed circuit board 54. Printed circuit board 54 may have one or more layers of dielectric material such as dielectric layers 54-1, 54-2, and 54-3 in the example of FIG. 3. Components 56 may be, for example, integrated circuits, discrete components such as capacitors, resistors, and inductors, switches, connectors, sensors, input-output devices such as status indicators lights, audio components, or other electrical and/or mechanical components for device 10. Components 56 may be attached to printed circuit 54 using solder, welds, anisotropic conductive film or other conductive adhesives, or other conductive connections. One or more layers of patterned metal interconnects 58 (i.e., copper traces or metal traces formed form other materials) may be formed within one or more dielectric layers in printed circuit board 54. Metal interconnects 58 may form signal lines that route signals between components 56.

Strain gauges may be implemented by mounting one or more packaged strain gauge devices to printed circuits such as printed circuit 54 of FIG. 3, as illustrated by mounted components 56. The mounting of packaged strain gauges to the surface of printed circuit board 54 will consume potentially scarce printed circuit real estate. Accordingly, it may be desirable to form one or more strain gauges from conductive traces 60 that are formed on one of the exposed surfaces of printed circuit board 54 or that are embedded within the interior of printed circuit board 54. In configurations in which strain gauge structures are embedded within printed circuit board 54, patterned metal traces may form strain gauges that are sandwiched between opposing dielectric layers in the printed circuit board (e.g., layers such as layers 54-1, 54-2, and 54-3). This embedded configuration may allow strain gauges to be formed fully or partly underneath the footprint of one or more of components 56 (i.e., the strain gauges may be overlapped by some or all of the outline of a component 56 when components 56 and printed circuit 54 are viewed in downward vertical direction –Z of FIG. 3).

Figure 4:
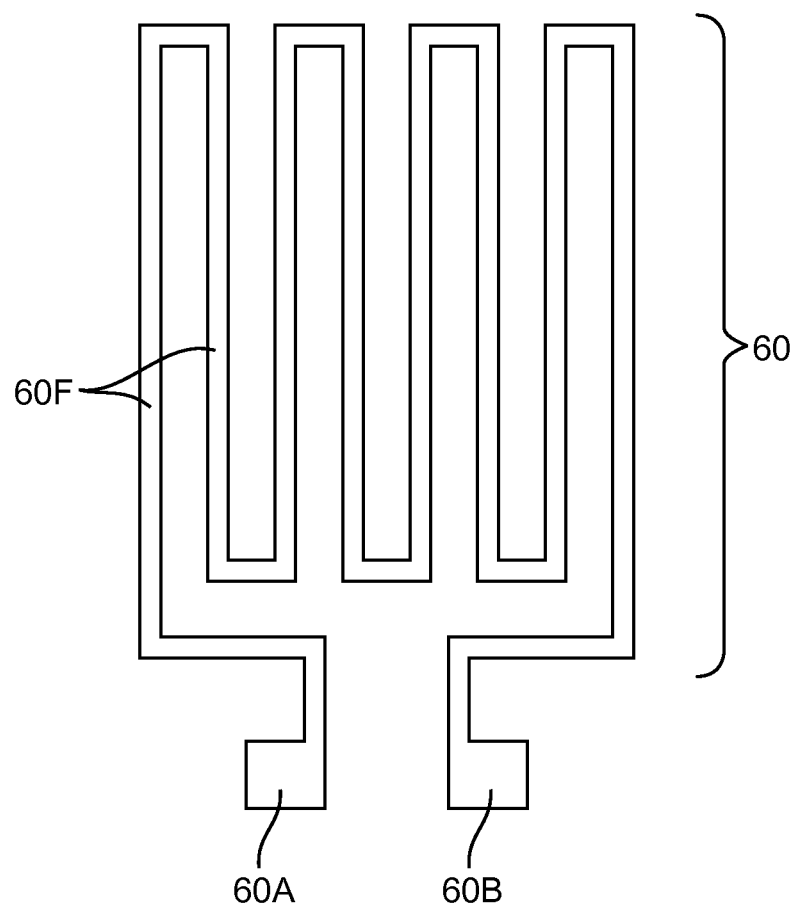
FIG. 4 is an illustrative strain gauge of the type that may be provided on a printed circuit substrate in accordance with an embodiment.

An illustrative configuration that may be used for strain gauges such as strain gauge 60 of FIG. 3 is shown in FIG. 4. As shown in FIG. 4, strain gauge 60 may include multiple parallel elongated metal strips, configured to form a single meandering path 60F coupled between terminals 60A and 60B. When printed circuit board 54 is subjected to stress (e.g., by bending during a drop event or other event that imparts stress onto printed circuit board 54), the resistance across terminals 60A and 60B will change. This change in resistance may be measured using a bridge circuit or other strain gauge circuitry.

Figure 5:
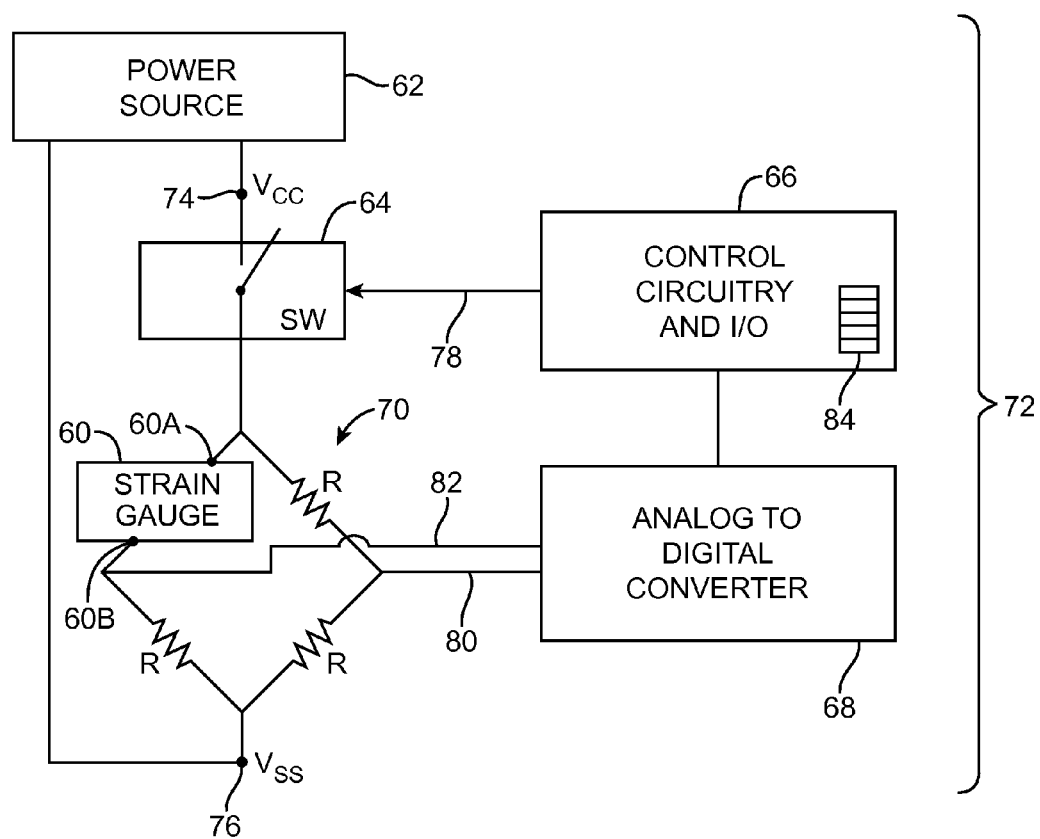
FIG. 5 is a circuit diagram of an illustrative strain gauge circuit that may be used in gathering stress information in an electronic device in accordance with an embodiment.

Illustrative strain gauge circuitry (stress data collection circuitry) 72 that may be used in making stress measurements in real time in device 10 is shown in FIG. 5. As shown in FIG. 5, strain gauge circuitry 72 may include strain gauge 60 (e.g., a strain gauge structure formed from a meandering metal trace of the type shown in FIG. 4 or other suitable strain gauge structure). The metal traces of strain gauge 60 may be formed on one of the surfaces of a printed circuit in device 10, may be embedded within the layers of a printed circuit in device 10, or may otherwise be incorporated into the structures of device 10 so that stresses experienced by the substrates, electrical components, and other structures of device 10 can be monitored.

Strain gauge 60 may be coupled into a bridge circuit such as bridge circuit 70. Power source 62 may produce a positive power supply voltage Vcc at a terminal such as positive power supply terminal 74. Power source 62 may produce a ground power supply voltage Vss at a terminal such as ground power supply terminal 76. Switch 64 may be controlled by control signals received from control circuitry and input-output circuitry 66 via a path such as path 78. When it is desired to make a stress measurement using strain gauge 60, control circuitry within control and input-output circuitry 66 (control circuitry 40 of FIG. 2) may generate a control signal on path 78 that directs switch 64 to change from a normally open state to a closed state. When switch 64 is closed, a voltage drop of Vcc-Vss will be applied across bridge circuit 70. Resistors R and the resistance of strain gauge 60 are configured to that analog-to-digital converter 68 will be provided with analog signals on input lines 80 and 82 that are proportional to stress in gauge 60. Analog-to-digital converter 68 digitizes these signals in real time and provides digital stress data to control circuitry and input-output circuitry 66.

Control circuitry and input-output circuitry 66 may include storage (e.g., storage and processing circuitry 40) such as buffer 84. Buffer 84 may be, for example, a circular buffer with sufficient storage to store 1-3 ms of stress data captured at a sample frequency of 200 kHz. Data capture may be initiated when a drop event is detected (e.g., using signals from a sensor such as an accelerometer). Stress data that has been collected in the circular buffer may be retained when an impact event is detected (e.g., based on accelerometer data or stress data exceeding a threshold). If desired, buffer 84 may have more or less storage and stress data may be captured at higher or lower frequencies. The use of a circular buffer with a 1-3 ms capacity for 200 kHz data is merely illustrative.

There may be one or more strain gauges 60 within device 10, each of which may be provided with strain gauge signal processing circuitry of the type shown in FIG. 5. The use of multiple strain gauges allows stress data to be captured for multiple locations within device 10, thereby providing a more comprehensive picture of the stresses experienced by the components within device 10. For example, the use of multiple strain gauges 60 may allow stress measurements to be made on multiple printed circuit boards, so that information can be gathered on the stress environment for components that are not all mounted on the same board. The use of multiple strain gauges 60 may also allow detailed stress profiles to be gathered for each printed circuit board. For example, by providing several strain gauges on a given printed circuit board, areas on the board at which stress becomes concentrated such as areas adjacent to fasteners can be accurately monitored. There may be one or more strain gauges on a printed circuit board, two or more strain gauges on a printed circuit board, three or more strain gauges on a printed circuit board, five or more strain gauges on a printed circuit board, or ten or more strain gauges on a printed circuit board.

Figure 6:
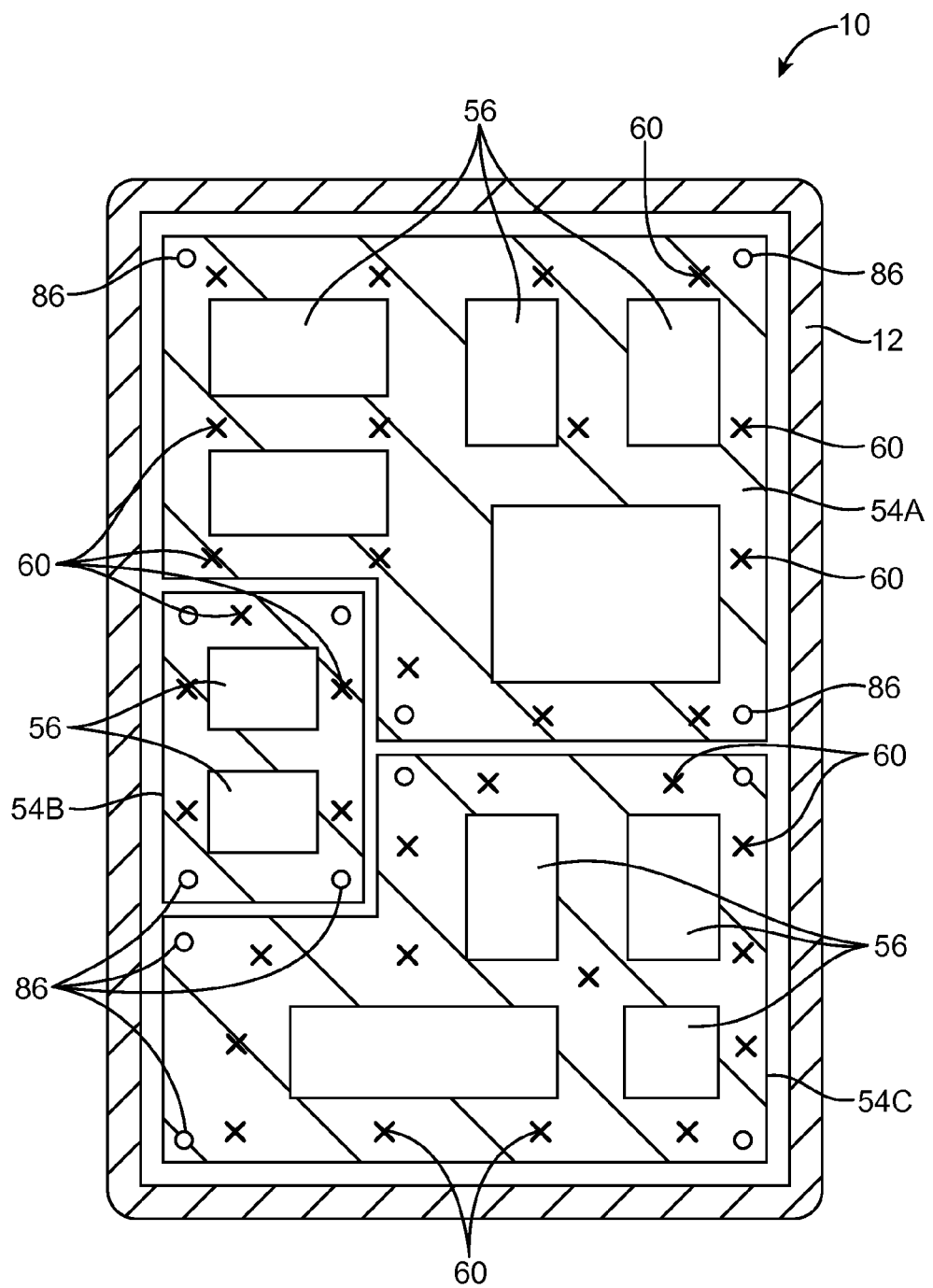
FIG. 6 is a top view of an illustrative set of printed circuit boards mounted within an electronic device housing showing illustrative locations at which stress sensors may be provided to monitor stress within the printed circuit boards in accordance with an embodiment.

FIG. 6 is a top view of an illustrative internal portion of device 10 showing where strain gauges 60 may be located (as an example). In the illustrative configuration of FIG. 6, device 10 has three printed circuit boards. A first set of components 56 has been mounted on printed circuit board 54A. A second set of components 56 has been mounted on printed circuit board 54B. Printed circuit board 54C contains a third set of components 56. Printed circuit boards 54A, 54B, and 54C may be mounted within device housing 12 using attachment structures 86. Attachment structures 86 may include screws or other fasteners, mounting posts, heat stakes, standoffs, welds, solder joints, adhesive, clips, or other structures for attaching printed circuit boards within housing 12. As shown in FIG. 6, strain gauges 60 may be distributed across printed circuit boards 54A, 54B, and 54C so as to provide a variety of stress measurement locations, including locations adjacent to attachment structures 86.

Figure 7:
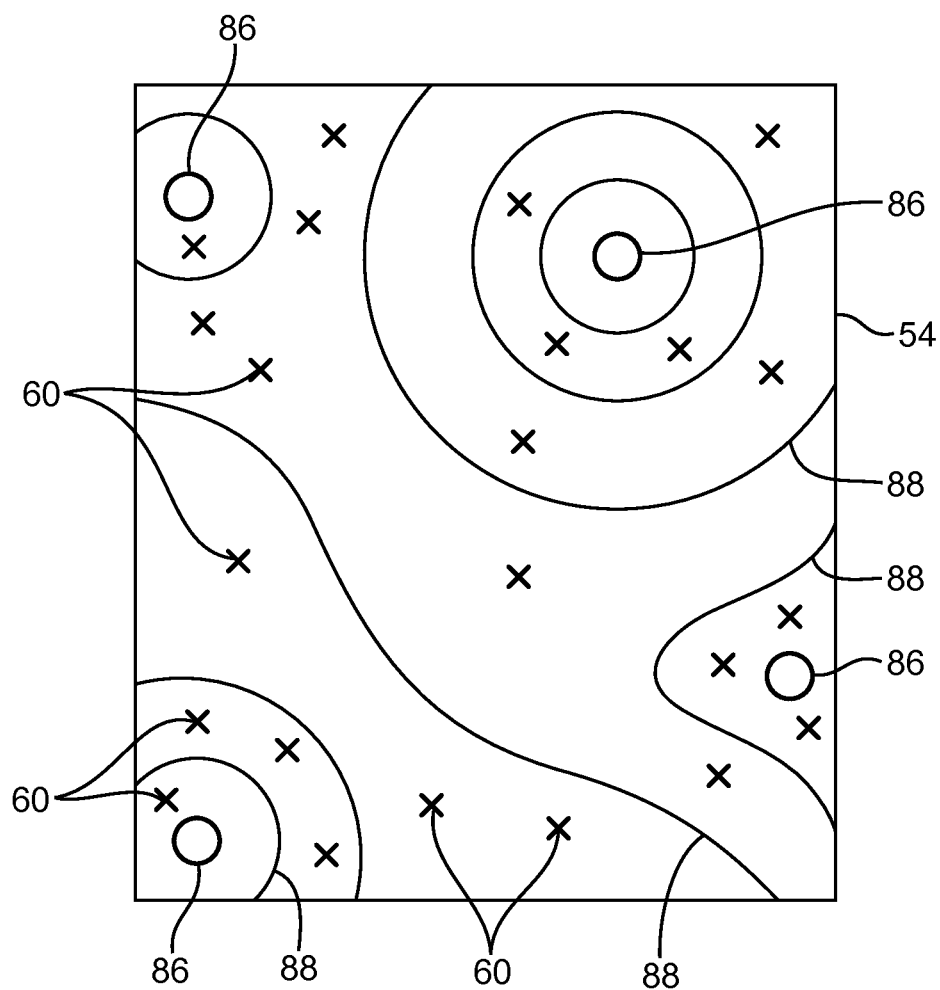
FIG. 7 is a top view of a printed circuit board showing how stress may be concentrated around mounting points at which the printed circuit board is mounted to a device housing using fasteners in accordance with an embodiment.

Stress isolines 88 on illustrative printed circuit board 54 of FIG. 7 illustrate how stress tends to be concentrated near attachment structures 86 (e.g., during impact events in which force is imparted to printed circuit board 54 via attachment structures 86). As a result, of the stress concentrations created by attachment structures 86 or other structures in device 10, a configuration of the type shown in FIG. 7 in which strain gauges 60 on printed circuit 54 are placed near the attachment structures 86 or other stress concentrators may be desirable to ensure accurate gathering of stress data. Configurations in which strain gauges 60 are arrayed on printed circuit boards such as printed circuit board 54 in a regular pattern of rows and columns and other types of configurations may be used if desired. The configuration of FIG. 7 is merely illustrative.

Figure 8:
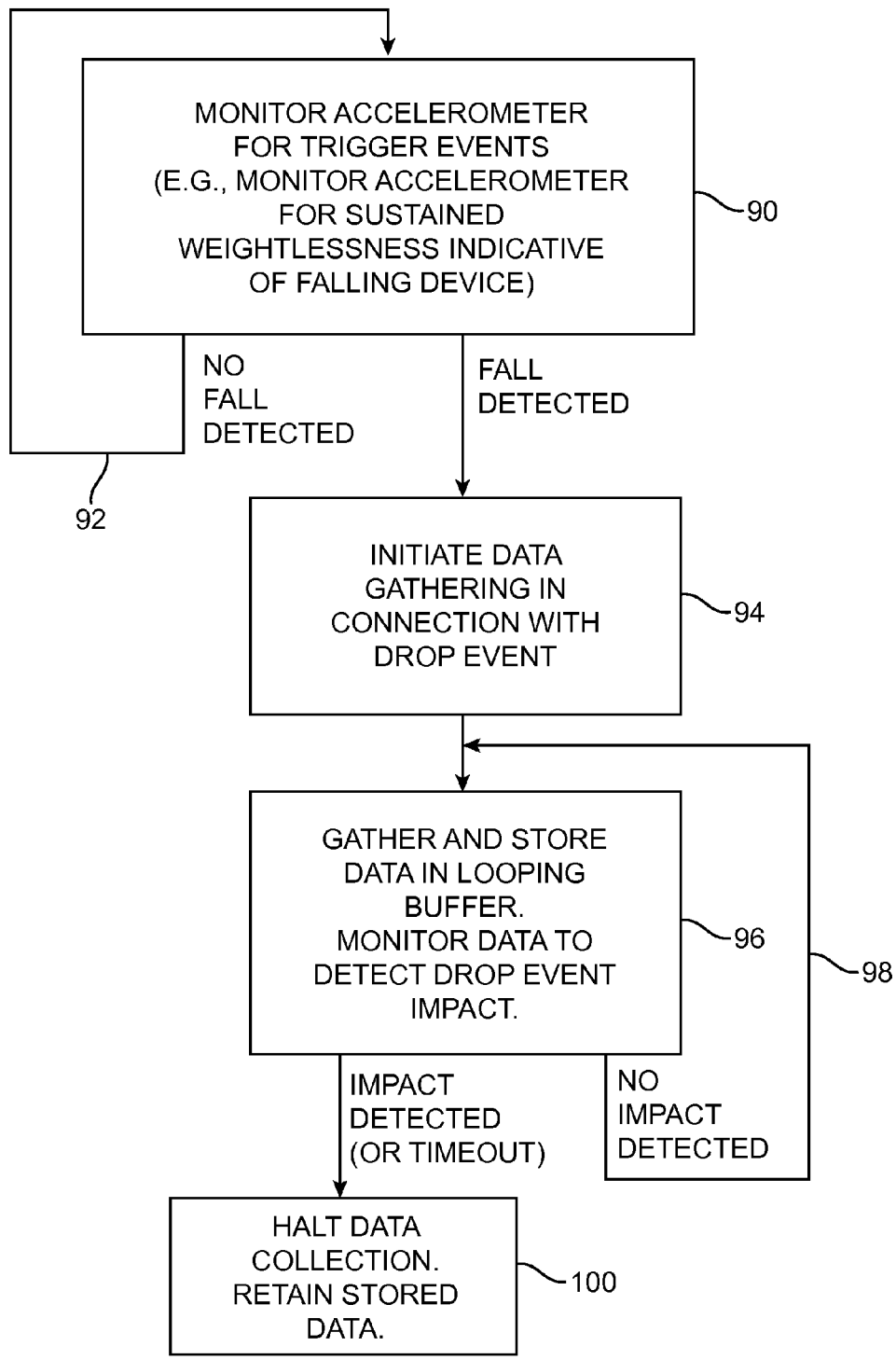
FIG. 8 is a flow chart of illustrative steps involved in gathering stress data from sensors in an electronic device such as an accelerometer and strain gauges on a printed circuit board in accordance with an embodiment.

FIG. 8 is a flow chart of illustrative steps involved in gathering stress data within device 10 using one or more strain gauges 60. During shocks such as shocks associated with drop events, stresses in device 10 may fluctuate rapidly. The time dependence of stresses in the time period immediately surrounding the drop event (e.g., in the 1-3 ms immediately after device 10 first contacts the ground) can provide valuable information. Accordingly, device 10 preferably captures and maintains stress information for this time period (or other suitable time surrounding the drop event). A stress sample acquisition frequency of about 200 kHz or other frequency (e.g., a frequency of over 50 kHz, a frequency more than or less than 200 kHz, etc.) may be used in gathering stress data.

In order not to consume more power than necessary by continually gathering high frequency stress data samples, stress data capturing operations may be limited in time. As an example, device 10 can initiate the stress data collection process using the stress data collection circuitry of FIG. 5 upon determining that a user has dropped electronic device 10. In particular, control circuitry 40 may, at step 90, monitor sensors such as accelerometer 48 (or other sensors that can detect motion of device 10 such as a gyroscope, a compass, etc.). If no period of sustained weightlessness is detected, device 10 can continue to monitor accelerometer 48 (or other sensors), as indicated by line 92. When a period of weightlessness is detected by accelerometer 48 (e.g., weightlessness for more than a predetermined amount of time T of about 1 microsecond to 1000 microseconds or other suitable time T), control circuitry 40 can conclude that device 10 is about to strike the ground or other surface and processing can begin collecting (storing) digital stress data from strain gauges 60 within circular buffer 84 (step 94).

During the operations of step 96, device 10 can continue to gather stress data from one or more strain gauges 60 and can store the gathered stress data in circular buffer 84. Once the capacity of buffer 84 has been reached, newly gathered stress data can be written on top of the oldest stress data in the circular buffer. This overwriting process can continue while device 10 monitors accelerometer 48 and/or strain gauge(s) 60 (or other sensors) for evidence of an impact associated with the drop event. The amount of time that lapses between when a drop event is first detected (i.e., when device 10 first becomes weightless) and when device 10 strikes the ground or other surface can vary depending on the location of device 10 relative to the ground and other environmental factors. It can therefore be difficult to determine how much time will elapse after weightlessness is detected before device 10 suffers an impact. Accordingly, device 10 preferably monitors data from accelerometer 48, strain gauge(s) 60, or other sensors to determine when device 10 has struck the ground or other external structure. So long as no impact is detected (e.g., so long as measured sensor data is less than a predetermined threshold), device 10 can continue to update the stress data stored in the circular buffer, as indicated by line 98.

When the accelerometer output from accelerometer 48, the stress data from strain gauge(s) 60, or other sensor data indicative of an impact between device 10 and an external surface exceeds a predetermined threshold amount, device 10 can conclude that device 10 has struck the ground or other external structure. In response to detection of an impact, device 10 can halt data collection in circular buffer 84 and can retain stored stress data for analysis (step 100).

To ensure that stress data associated with the impact event is satisfactorily recorded, device 10 can wait for a predetermined amount of time after impact has been detected before halting stress data capturing operations. As an example, if circular buffer 84 is sufficiently large to store 2 ms of stress data without overwriting older stress data, device 10 can, upon detection of an impact by measuring an accelerometer output signal that is larger than a predetermined amount, store an additional 1.9 ms of stress data in circular buffer 84. In this example, about 0.1 ms of data before the detected beginning of the impact will be retained (e.g., to help ensure that details on the moment of impact are not lost due to processing delays). After the predetermined amount of time after impact has passed (i.e., after 1.9 ms has elapsed in the present example), the control circuitry of device 10 can halt further stress data collection and can retain the stored data in circular buffer 84 for further analysis. If desired, device 10 may include sufficient memory to implement multiple circular buffers. With this type of approach, data from more than one drop event can be stored.

The stress data that is collected may be collected from one or more strain gauges. As an example, the stress data that is collected may include stress data from each of strain gauges 60 in FIG. 6. Stress data may be analyzed by device 10 in real time or may be analyzed by device 10 or other equipment at a later time. Stress data analysis may be performed to develop a map of stress values across the surface of a printed circuit board (e.g., to develop stress isolines such as isolines 88 of FIG. 7), may be analyzed to determine how much stress each of components 56 has been subjected to, may be analyzed to identify areas of printed circuit boards and particular electrical components that have been subjected to excessive stress, may be analyzed to identify regions in which stress changed rapidly as a function of time, or may be analyzed to produce other information about the location, magnitude, and duration of stress in printed circuit board 54, components 56, and other structures in device 10.

Figure 9:
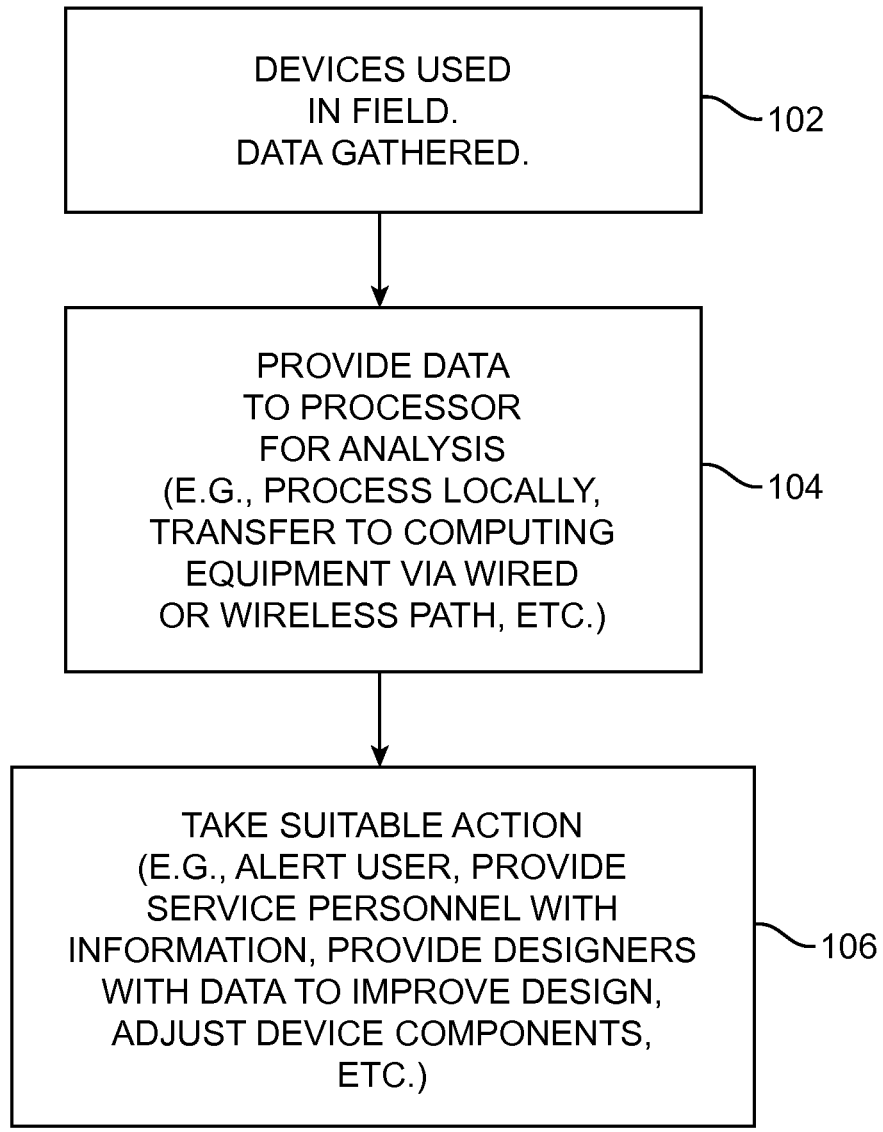
FIG. 9 is a flow chart of illustrative steps involved in analyzing stress data gathered by sensors in an electronic device during use of the electronic device in accordance with an embodiment of the present invention.

FIG. 9 is a flow chart of illustrative operations involved in using strain gauges 60 to collect stress data and in taking appropriate action in response to collected stress data.

At step 102, device 10 may be used in the field by a user. Device 10 may be operated normally to perform functions such as supporting cellular telephone calls, web browsing, email, and other communications functions and operations for a user. If desired, device 10 may be operated in a testing environment by robotic testing equipment and test personnel. An advantage of allowing users to operate devices in the field is that this allows stress data to be collected in real life conditions rather than in a simulated environment. Accordingly, illustrative scenarios in which device 10 is operated normally by a user (e.g., in a home, office, or other indoor or outdoor environment) may sometimes be described herein as an example.

During the use of device 10 at step 102, printed circuit boards 54, components 56, and other structures in device 10 may be subjected to stresses. If desired, the strain gauges in device 10 may be used to periodically gather stress data for further analysis and/or for taking actions in real time. Preferably, device 10 monitors a sensor such as accelerometer 48 to detect initiation of a drop event and, upon detecting a drop event or other impact event, gathers and retains stress data, as described in connection with FIG. 8.

At step 104, collected stress data can be analyzed. Stress data may be analyzed internally by device (e.g., in real time or later such as when a user requests stress-related information) or may be analyzed by external equipment. As an example, external equipment 42 and device 10 may communicate over communications path 44. While communicating, device 10 may provide the collected stress data in device 10 to external equipment 42 (e.g., over a wired and/or wireless path such as path 44 of FIG. 2). External equipment 42 may be, for example, a server or other computing equipment associated with a manufacturer (e.g., computing equipment that receives data over the Internet) or may be a desktop or laptop computer to which device 10 is connected with a cable or a wireless local area network. Once the stress data that device 10 has collected has been provided to external equipment 42, external equipment 42 can analyze the stress data.

At step 106, actions may be taken based on the analyzed data. For example, device 10 may produce real time alerts or may produce logs or other reports containing diagnostic information that can serve as repair advice, historical data that may be used during debugging and design updating, and other analysis results.

If desired, device 10 can analyze stress data whenever a drop event results in the capture and storage of stress data. If analysis reveals that the total amount of stress was high, device 10 can issue an alert to the user. For example, device 10 can display a message such as "this device has been subjected to an unexpected drop event, please contact customer service for more information." The alert can be issued when the drop even occurs or at a later time.

Device 10 may also maintain a log or other report of stresses that have been measured. The user of device 10 or a technician can retrieve the log to ascertain the nature of the stresses that printed circuit boards and electrical components in device 10 have experienced. The stress report may contain time dependent stress magnitudes experienced by each of the strain gauges 60, may present data in the form of two-dimensional or three-dimensional graphs illustrating where stresses of various levels have been measured, may identify particular components that have been subjected to excessive stress (e.g., "the microprocessor in this device has experienced excessive stress due to a drop event") or may otherwise quantify and describe the nature of the stresses measured by device 10. If desired, the log or other stress report may provide historical stress data (i.e., "this device has been dropped 13 times").

The manufacturer of device 10 may use report data to identify possible future design modifications. For example, if the report data indicates that a particular electrical component is experiencing more stress than other components during drop events, the printed circuit board layout can be revised so that the heavily-stressed component is located farther from the high stress region. The sources of component failures can also be investigated using the report data.

Service personnel at a service center can review stress report data for assistance with diagnosing problems and making repairs. If, for example, a report shows that one component has experienced considerably more stress than other components, service personnel may be informed and may use this information to replace or otherwise repair that component or to make adjustments to the affected component. The stress report data can therefore help the service personnel make repairs efficiently.

If desired, data from other sensors may be retained within device 10. As an example, accelerometer data may be captured and retained in connection with a drop event or other activities. The accelerometer data may be used alone or in combination with other data such as stress data from strain gauges 60 to evaluate the nature of impacts during drop events. If desired, accelerometer data may be used to detect a drop event and, once the drop event has been detected, accelerometer data may be captured at a high frequency (e.g., 200 kHz) and stored in circular buffer 84 until data collection is halted due to a detected impact. Additional sensor data such as compass data, gyroscope data, and other sensor data can also be stored in circular buffer 84.

The foregoing is merely illustrative and various modifications can be made by those skilled in the art without departing from the scope and spirit of the described embodiments. The foregoing embodiments may be implemented individually or in any combination.

What is claimed is:

1. An electronic device, comprising:
   an accelerometer;
   storage; and
   circuitry that is configured to detect whether the electronic device has been dropped based on data from the accelerometer and, in response to determining that the electronic device has been dropped, storing data in the storage, wherein the data comprises stress data and wherein the electronic device further comprise at least one strain gauge that generates the stress data, wherein the storage comprises a circular buffer, wherein the circuitry is configured to collect the stress data in the circular buffer.

2. The electronic device defined in claim 1 further comprising a printed circuit board, wherein the strain gauge comprises metal traces supported by the printed circuit board.

3. The electronic device defined in claim 2 wherein the printed circuit board comprises multiple dielectric layers and wherein the metal traces comprise a meandering trace embedded within the dielectric layers.

4. The electronic device defined in claim 1 wherein the circuitry is configured to detect when the electronic device has impacted an external surface and wherein the circuitry is configured to halt collection of the stress data in the circular buffer in response to determining that the electronic device has impacted the external surface.

5. The electronic device defined in claim 1 wherein the at least one strain gauge comprises a plurality of strain gauges.

6. The electronic device defined in claim 5 further comprising a printed circuit board having dielectric layers, wherein the plurality of strain gauges are sandwiched between the dielectric layers.

7. The electronic device defined in claim 6 wherein the printed circuit board comprises attachment features, and wherein the plurality of strain gauges are concentrated near attachment structures.

8. A method of gathering information on operation of an electronic device by a user, wherein the electronic device comprises a printed circuit board, at least one strain gauge, and a switch interposed between the at least one strain gauge and a power source, and wherein the switch has an open position and a closed position, the method comprising:
   with an accelerometer in the electronic device, monitoring the electronic device to determine whether the electronic device has been dropped; and
   in response to determining that the electronic device has been dropped, directing the switch to change from the open position to the closed position and collecting stress data in the electronic device.

9. The method defined in claim 8 wherein printed circuit board comprises dielectric layers and wherein collecting the stress data comprises:
   collecting the stress data with the at least one strain gauge sensor embedded between the dielectric layers.

10. The method defined in claim 8 wherein the printed circuit board comprises dielectric layers and wherein collecting the stress data comprises:
    collecting the stress data with the at least one strain gauge sensor embedded within the dielectric layers, wherein the at least one strain gauge sensor comprises a plurality of strain gauge sensors.

11. The method defined in claim 10 further comprising collecting the stress data in storage in the electronic device.

12. The method in claim 11 further comprising:
determining whether the electronic device has struck an external surface; and
halting the collection of the stress data in response to determining that the electronic device has struck the external surface.

13. The method defined in claim 12 wherein determining whether the electronic device has struck the external surface comprises determining whether data from the accelerometer has exceeded a predetermined threshold.

14. The method defined in claim 12 wherein determining whether the electronic device has struck the external surface comprises determining whether the stress data has exceeded a predetermined threshold.

15. The method defined in claim 8 further comprising:
providing the collected stress data to external equipment over a communications path.

16. A method of operating an electronic device with a display, the method comprising:
with an accelerometer in the electronic device, monitoring the electronic device to determine whether the electronic device has been dropped;
in response to determining that the electronic device has been dropped, collecting stress data in the electronic device;
after collecting stress data in the electronic device, analyzing the stress data;
in response to analyzing the stress data, displaying an alert on the display.

17. The method defined in claim 16, wherein displaying the alert on the display comprises displaying a graph illustrating where stresses of various levels were experienced when the electronic device was dropped.

18. The method defined in claim 16, wherein displaying the alert on the display comprises identifying a component in the electronic device that was subjected to a high amount of stress when the electronic device was dropped.

19. The method defined in claim 16, wherein displaying the alert on the display comprises providing historical stress data.

20. The method defined in claim 19, wherein the historical stress data comprises a number of times the electronic device has been dropped.

* * * * *